United States Patent [19]
Fulton, III

[11] Patent Number: 6,053,870
[45] Date of Patent: Apr. 25, 2000

[54] ULTRASONIC VISIBLE SURGICAL NEEDLE

[75] Inventor: Richard Eustis Fulton, III, Grand Junction, Colo.

[73] Assignee: AngioDynamics, Inc., Queensbury, N.Y.

[21] Appl. No.: 09/186,739

[22] Filed: Nov. 5, 1998

Related U.S. Application Data

[60] Provisional application No. 60/064,966, Nov. 8, 1997, and provisional application No. 60/067,879, Dec. 8, 1997.

[51] Int. Cl.⁷ .................................................. A61B 8/00
[52] U.S. Cl. ............................................................ 600/458
[58] Field of Search ................................ 128/6, 329, 754; 600/464, 437, 459, 461; 604/164

[56] References Cited

U.S. PATENT DOCUMENTS

| | | |
|---|---|---|
| 4,401,124 | 8/1983 | Guess et al. . |
| 4,566,438 | 1/1986 | Liese et al. ................... 128/6 |
| 4,582,061 | 4/1986 | Fry .......................... 128/654 |
| 4,799,495 | 1/1989 | Hawkins et al. ........... 604/164 |
| 4,869,259 | 9/1989 | Elkins ....................... 128/660 |
| 4,977,897 | 12/1990 | Hurwitz . |
| 4,986,279 | 1/1991 | O'Neil ...................... 604/164 |
| 5,048,530 | 9/1991 | Hurwitz . |
| 5,081,997 | 1/1992 | Bosley, Jr. et al. . |
| 5,213,569 | 5/1993 | Davis . |
| 5,221,269 | 6/1993 | Miller et al. . |
| 5,383,466 | 1/1995 | Partika . |
| 5,490,521 | 2/1996 | Davis et al. . |
| 5,611,345 | 3/1997 | Hibbeln . |
| 5,766,135 | 6/1998 | Terwilliger . |
| 5,769,795 | 6/1998 | Terwilliger . |

*Primary Examiner*—William E. Kamm
*Assistant Examiner*—Maulin Patel
*Attorney, Agent, or Firm*—McAulay Nissen Goldberg Kiel & Hand, LLP

[57] ABSTRACT

Transverse notches in a surgical needle provide an increased reflecting area and enhanced response to ultrasonic probing to provide an enhanced image on an ultrasonic echo sensor. Having the notch cut through to the needle lumen entrains small air bubbles in the notch further enhancing ultrasonic reflection and ultimate imaging of the needle's position.

16 Claims, 3 Drawing Sheets under US Patent 6,053,870

ULTRASONIC VISIBLE SURGICAL NEEDLE

REFERENCE TO RELATED APPLICATIONS

This application claims the priority of Provisional Applications, Ser. No. 60/064966 filed on Nov. 8, 1997 and Ser. No. 60/067879 filed on Dec. 8, 1997.

BACKGROUND OF THE INVENTION

This invention relates to a medical device that provides enhanced image and response to an ultrasound signal and more particularly to a surgical needle having geometric features that provides an enhanced image and response.

Ultrasonic imaging has long been used in medical practice to provide images not only of body organs and parts but also of the medical instruments and in particular needles that are used in connection with various medical procedures.

For example, ultrasonic imaging is used to guide a medical needle into a body part to effect a biopsy, to access fluid collection for sampling or drainage, to obtain vascular access and to access the urinary and biliary tracts. Ultrasonic imaging is also used to place a needle at a tumor or other body structure for subsequent surgical removal.

A major limitation on the ultrasonic guided intervention or procedures are the inability to image the medical instrument or needle adequately in many circumstances. The visibility of the needle is strongly dependent on the particular geometrical relationship between the transducer that provides the ultrasonic beam and the reflective surface of the instrument. The amount of ultrasonic energy reflected from the instrument toward the transducer (an ultrasonic echo sensor) determines the quality of the image of the instrument on the monitor. If the needle is in the plane of the interrogating ultrasonic beam and horizontal to the face of the sensing transducer, or perpendicular to the direction of the incident beam, the reflected energy is optimized and a usable visible image is obtained. However, as the needle becomes less perpendicular to the direction of the incident beam, lesser amounts of ultrasonic energy are reflected to the sensor and the instrument is imaged poorly or not at all.

The optimal geometric relationship is difficult to maintain in all but fairly limited applications of ultrasonic guided interventions. It becomes nearly impossible to maintain the optimum geometry in many instances because of intervening organs or structures. This results in poor visualization of the instrument, procedure time is lengthened and complexities are created which would not be present if the needle were easily seen.

Multiple passes with a needle may have to be made before it can be visualized causing tissue damage within adjacent organs or structures and creating the potential of bleeding and other complications. There are times when the physician is able to visualize the target lesion quite well but not the needle or other instrument. Moving the sensing transducer can result in the needle being imaged but the image of the target lesion is lost. A series of trial and error maneuvers are employed. Breathing motion of the patient further complicates the process.

This problem has been addressed by a large number of proposed designs, including those shown in U.S. Pat. No. 4,869,259, No. 4,977,897, No. 5,048,530, No. 5,081,997, No. 5,213,569, No. 5,221,269, No. 5,383,466, No. 5,490, 521, No. 5,611,345, No. 5,766,135 and No. 5,769,795.

The devices shown in the above referenced patents are intended to enhance ultrasonic visibility. Some of these devices are complex and expensive to manufacture. Some of these devices are difficult to manipulate within the patient such as the square rectangular shaped needle suggested in U.S. Pat. No. 5,611,345. Furthermore, many of the devices only marginally enhance ultrasonic visibility.

Accordingly, it is an object of this invention to provide a design for a medical instrument and in particular a needle which will provide enhanced imaging in a wide range of orientations between the axis of the needle and the ultrasonic echo sensor.

It is a further and related object of this invention to provide this enhanced imaging in a design that is simple and inexpensive to manufacture and relatively simple to operate.

These two objects are important in order to assure maximum usage of the invention in a large number and a wide variety of applications where an ultrasonically identified needle is important.

Furthermore, it is another related purpose of this invention to provide the above objectives in a design which provides no additional risk of trauma to tissue.

There are inevitable trade-offs to the design considerations to achieve the above interrelated objectives. Addressing all of these considerations calls for some tradeoff between the objectives.

Accordingly, it is a major object of this invention to provide an enhanced ultrasonically visible needle which achieves the objectives of low cost, simple structure, high visibility, high degree of safety and avoids complicated procedures or new techniques with which medical personnel are not familiar.

Most particularly, it is an object of this invention to achieve all of these objects with an enhanced trade-off value for the combined objectives.

BRIEF DESCRIPTION

In brief, one embodiment of this invention is a surgical needle manufactured of stainless steel or some other material which provides an interface with human tissue that results in an ultrasonic echo. One or more transverse notches are cut into the sidewall of the needle. In one tested embodiment, the transverse notch intersects the circumference of the needle over approximately 100°. Thus the notch cuts through to the lumen. The notch is a wedge-shaped notch defining first and second oblique walls in the sidewall of the lumen. Where these walls are planar, the plane of each wall intersects the axis of the needle at an acute angle. The acute angle may range from 15° to 75° and in a preferred embodiment are each 45°. The walls created by the notch provide a large amount of reflective surface area.

In operation, when the needle is inserted into a patient, the surface of the needle will reflect incident ultrasonic energy in directions that are determined by the needle sidewall and the two notch walls. The result is to reflect ultrasonic energy at a substantial range of angles. When the needle is inserted into a patient, sufficient air is inevitably entrained so as to provide small air bubbles which form on or are trapped in the notches. These air bubbles provide a further sound velocity contrast with tissue so as to enhance wide angle reflection of an incident ultrasonic energy pulse. In this fashion, the ultrasonic echo sensor can have a wide variety of spatial orientations relative to the needle and yet receive a strong enough ultrasonic echo to provide a usable and useful image of the needle.

DESCRIPTION OF THE PREFERRED EMBODIMENTS

Figure 1:
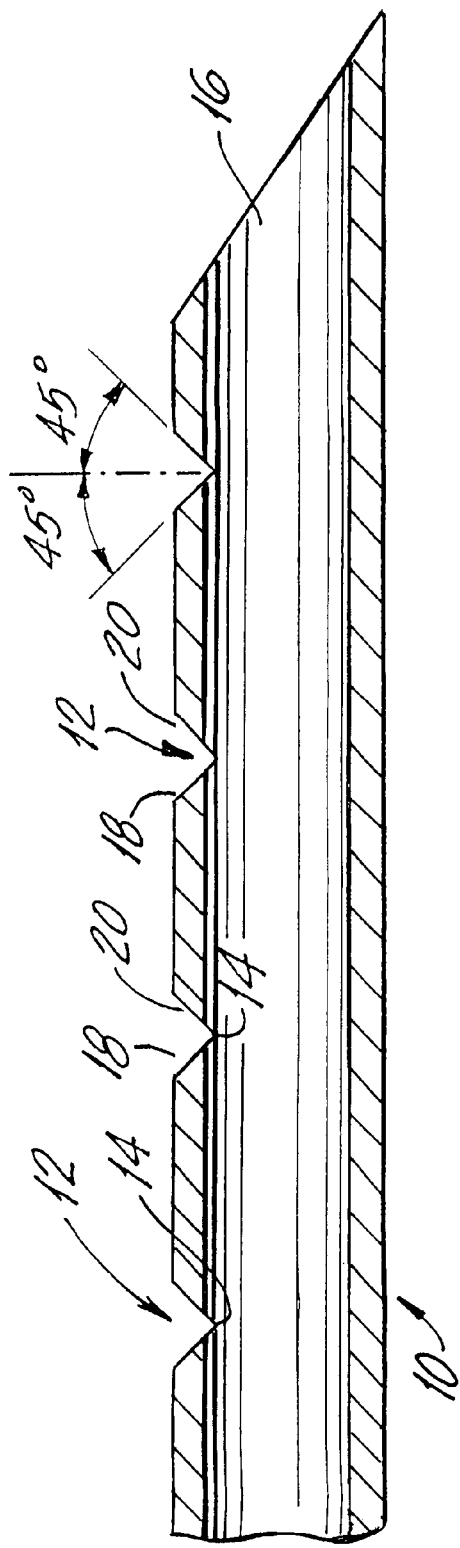
FIG. 1 is a longitudinal sectional view of one embodiment of this invention showing a particular notch arrangement at the distal portion of a needle; the planes of the notch faces 18 and 20 being at 450 to the lumen axis.
Figure 2:
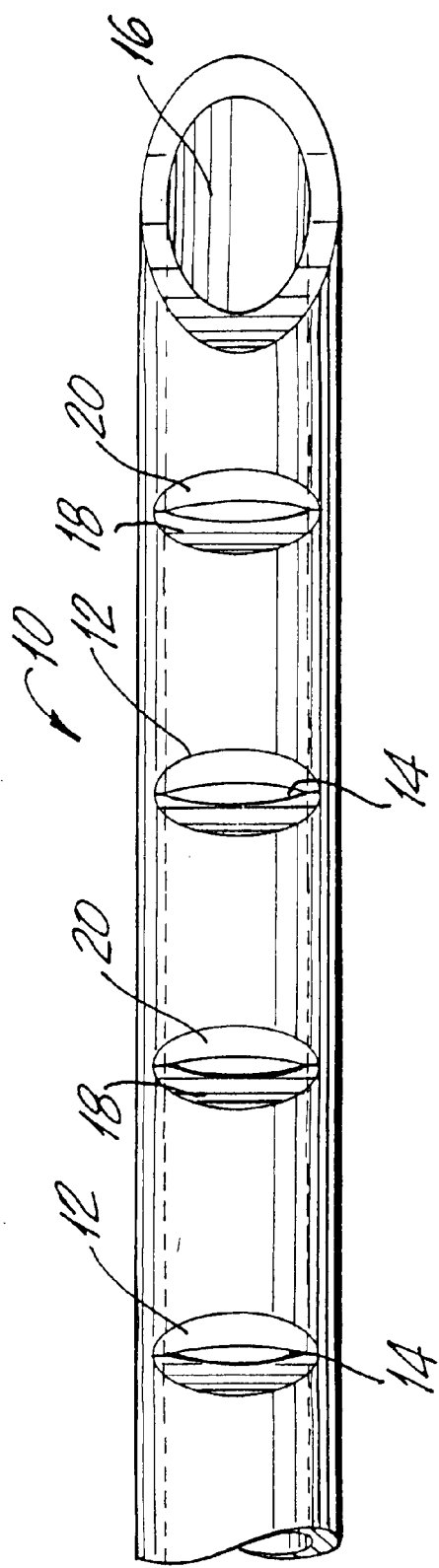
FIG. 2 is a plan view of the FIG. 1 needle.

The FIG. 1 embodiment shows a surgical needle 10. A series of transverse notches 12 near the distal end of the needle extend around substantially less than half the circumference of the needle. Each notch 12 is cut deep enough so that over a small distance, there is an opening 14 which provides communication between the lumen 16 of the needle and the zone defined by the notch.

The notch 12 is cut with the two notch walls at an angle of 90° to one another. The plane of each of the notch walls 18, 20 are at an angle of 45° to the axis of the lumen 16. These two wall faces 18, 20 provide a relatively significant area to reflect incidence of ultrasonic energy and thus create an ultrasonic echo that can be received over a substantial area. It has an amplitude significant enough to provide the desired image on an appropriate monitor or other imaging device.

In addition, the opening 14 tends to permit a certain amount of air to be trapped within the notch. Thus air, trapped as small bubbles of air, causes a further significant ultrasonic reflection to the sensor that substantially enhances the image as presented to the physician.

Figure 3:
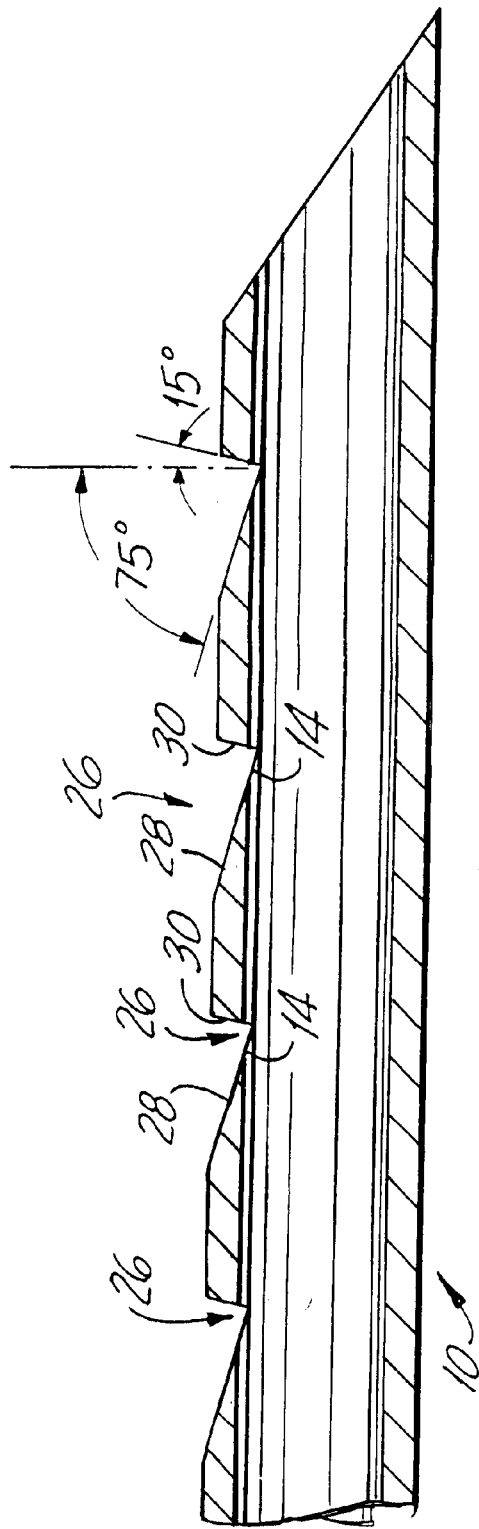
FIG. 3 is a longitudinal view similar to that of FIG. 1 showing a second embodiment in which the plane of the notch faces are at different angles to the axis of the lumen.
Figure 4:
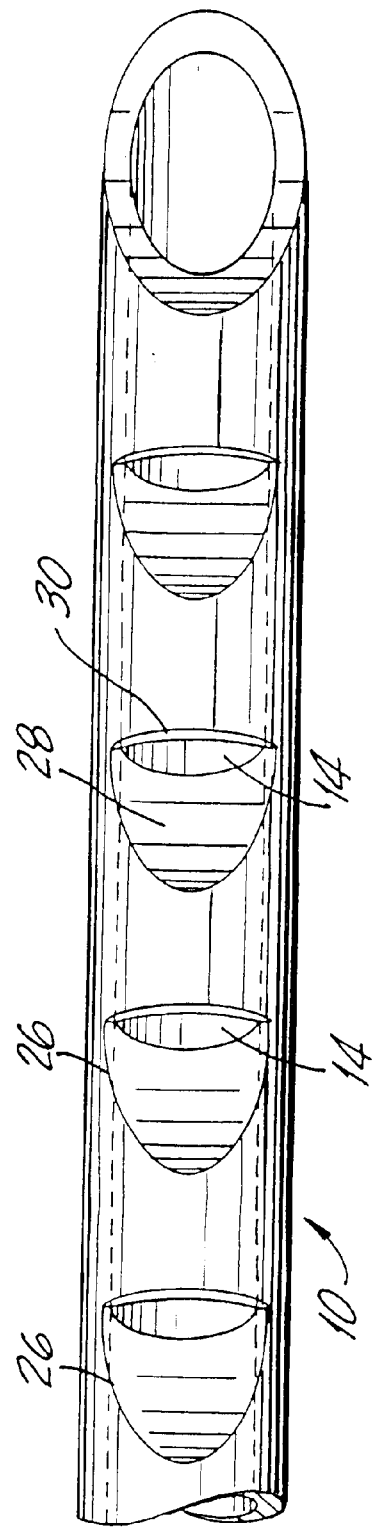
FIG. 4 is a plan view of the FIG. 3 needle.

In the FIG. 3 embodiment, notches 26 are cut to provide a first notch wall 28 having an angle of 15° with the lumen axis and a second notch wall 30 having an angle of 75° with the lumen axis. The notch wall 30 faces proximally so that energy reflected from the wall 30 will be directed toward an echo sensor transducer placed near the hub of the needle.

The relative angles of the two notch wall faces may be established as a function of the particular application of the invention and, most significantly, as a function of the location of the sensor that receives the ultrasonic echo.

It is believed that the larger the face of the notch wall that looks back to the sensor, the more effective the invention will be in providing a useful image to the physician. It could well be that a curved notch wall would be effective providing that the surface of the curvature defined by the notch wall intersects the axis of the lumen at an acute angle; where the acute angle is sufficiently small to assure a substantial reflecting wall surface that faces toward the sensor being employed.

The position of the transducer and the direction of the sonar pulses will not usually be uniquely determined with respect to the axis of the needle. Accordingly, it is presently preferred to have the walls of each of the two notches 18 and 20 to be at an angle of 45° to the axis of the needle; in particular, one is at an angle of plus 45° and the other is at an angle of minus 45°. This should provide the needle with the greatest range of reflection.

However, in order to increase the angles covered by the reflected beams, it is contemplated that multiple notches might be employed in which the angle of the sidewalls of the notches will differ from notch to notch so that one sidewall may be at 15° to the axis, another at 30° and another at 45°.

Figure 5:
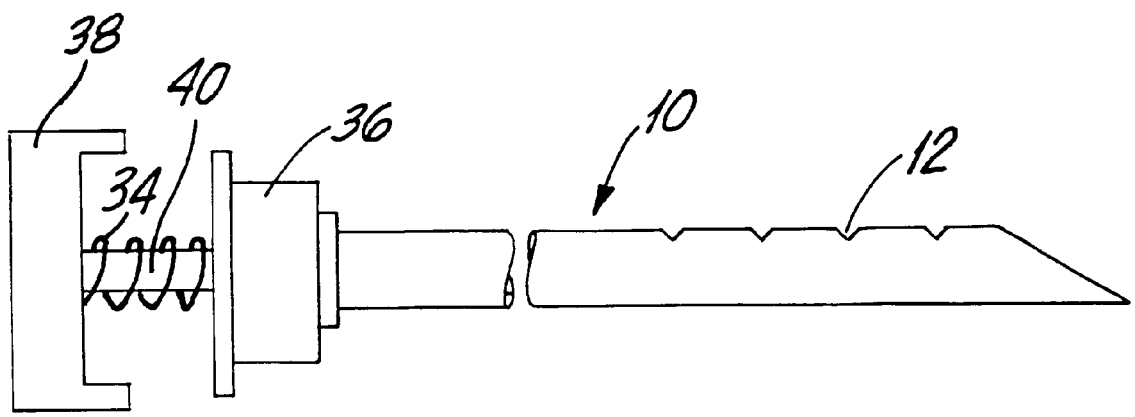
FIG. 5 is a mechanical schematic showing the arrangement of a manually operable spring loaded stylet that can be employed within the needle of this invention to assure the trapping of air bubbles in the notch.

As shown in FIG. 5, a spring 34 placed between the hub 36 of the needle and the hub 38 of a stylet 40 permits the stylet to be pumped with finger pressure. The pumping motion will cause turbulence in the fluid surrounding the needle which is immediately adjacent to the notches thereby enhancing the image provided to the physician.

The opening 14 has the advantage of providing air bubbles. This advantage may be further enhanced by removing and reinserting the stylet 40 to thereby push trapped air into the notches.

The nature of the opening 14 is sufficiently small and can be made sufficiently small so that liquid administered through the needle or aspirated from the needle will not come through the opening 14.

This opening 14 provides the appreciable advantage of permitting the trapping of air in the notch to enhance visibility without creating any risk of compromising the performance of the needle.

It is generally desired to keep the circumferential arc of the notches 12, 26 to as little as possible to be consistent with providing the small opening 14. In this fashion, the sidewall strength of the needle is minimally compromised.

The circumferential arc over which the notch is cut is essentially a function of the outer radius R of the needle and the wall thickness T of the needle. A notch cut to communicate to the lumen is a function of the ratio: (R−T)/R. Specifically, the circumferential arc that provides a notch which just meets the lumen, is an angle that is twice the angle having the cosine (R−T)/R. The bigger the wall thickness T, the smaller the ratio and the bigger the angle having that cosine. In formula terms, the circumferential arc angle "A" which must be exceeded to communicate with the lumen is:

$$A = 2[\cos^{-1}(R-T)/R]$$

For example, a 22 gauge needle will have an O.D. of 28 mils (0.028 inches) and thus an R of 14 mils. It may have a wall thickness T of 4 mils. This provides a ratio of (14−4)/14, which equals 0.7143. The angle having a cosine of 0.7143 is about 44.5°. Thus the notch for such a needle will encompass an arc of needle circumference greater than 89°. Generally, the embodiments of this invention will have notches that encompass less than 120° of needle circumference in order to insure communication with the lumen.

It may even be desirable to cut the notch with a laser beam so as to provide a somewhat curved obliquely positioned notch in the sidewall with an optimum trade-off of as much reflective surface area as possible with as little needle strength compromised as possible.

Experimental needles having notches in accordance with the teachings of this invention have been tested in a laboratory situation and found to have sufficient rigidity so that the structural integrities are not compromised by the notches. It is believed that any notch which would extend close to 180° around the circumference of the sidewall would tend to reduce structural integrity.

As indicated above, by incorporating multiple air bubbles in the notches, there would be a substantially expansion on the angles covered by the reflective surfaces.

Although tests have been made showing the effectiveness of a needle having the design shown herein, it is believed that it is the combination of the angle or oblique sidewalls together with the air bubbles in the notch that provide the highest enhancement of imagery.

As may be appreciated, for the reasons indicated above, the structure of this invention provides an optimized trade-off of providing enhanced echo image while minimizing degradation to either the structural strength of the needle or the functional performance of the needle.

Although this invention has been described in connection with particular embodiments, it should be understood that there would be variations on the embodiment shown which would provide the advantage of the invention that are included in the teachings herein.

For example, reference is made throughout the specification in claims to a needle. However, it is conceivable that there may be certain situations in which some cannula other than a needle would advantageously employ the arrangement of this invention. It should be understood herein that a needle is defined to include such cannulas.

Although the two notch walls are shown at an angle of 90° to one another, they need not be at 90° to each other in order to provide the effect of this invention. Nor, need the notch wall angles equal one another. The angle of each of the two notch walls to the lumen axis is selected to optimize reflecting ultrasonic energy.

The preferred embodiments show communication of the notches 12 and lumen 16 through the opening 14. However, it is contemplated that the notch itself, even if not cut through to the lumen, will provide enhanced ultrasonic visibility because of the surface area of the notches and the oblique angling of those surfaces.

The introduction of air into the notches 12 might be accomplished by placing a diaphragm with a small hole in it over the entry to the lumen at the hub. The physician could place a thumb on the hole and pump air within the lumen into the notches.

What is claimed is:

1. A surgical needle visible to ultrasound comprising:
    a tubular sidewall defining a lumen and having an axis, said sidewall having at least one transverse notch that intersects said sidewall over less than 180° of the circumference of the sidewall, said notch having a first face, there being an acute angle relationship between a substantial portion of said first face and lines parallel to said axis.

2. The surgical needle of claim 1 wherein:
    at least a portion of said notch extends through said sidewall to said lumen of said needle to provide communication between said notch and said lumen.

3. The surgical needle of claim 1 further comprising a plurality of said notches.

4. The surgical needle of claim 2 further comprising a plurality of said notches.

5. The surgical needle of claim 2 wherein: said notch intersects the sidewall of the needle over less than 120° of the circumference of the needle.

6. The surgical needle of claim 4 wherein: each of said notches intersects said sidewall of the needle over less than 120° of the circumference of the needle.

7. The surgical needle of claim 1 wherein: said notch has a second face, there being an acute angle relationship between a substantial portion of said second face and lines parallel to said axis.

8. The surgical needle of claim 7 wherein: each of said first and second faces are flat faces and wherein said acute angle relationships are between 15° and 75°.

9. The surgical needle of claim 2 wherein: said notch has a second face, there being an acute angle relationship between a substantial portion of said second face and lines parallel to said axis.

10. The surgical needle of claim 9 wherein: each of said first and second faces are flat faces and wherein said acute angle relationships are between 15° and 75°.

11. The surgical needle of claim 3 wherein: each of said notches has a second face defining a surface having a substantial part thereof that intersects a line parallel to said axis at an acute angle.

12. The surgical needle of claim 11 wherein: each of said first and second faces are flat faces and wherein said acute angles are between 15° and 75°.

13. The surgical needle of claim 2 further comprising:
    a finger actuated spring loaded stylet in said lumen of said tubular sidewall.

14. The surgical needle of claim 13 wherein: said stylet has a hub, said needle has a hub and said spring is positioned between said hubs.

15. The method of enhancing the visibility of a surgical needle having a lumen comprising the step of:
    introducing air bubbles into the notch of claim 2.

16. The method of claim 15 wherein said step of introducing air bubbles includes introducing a stylet into the lumen of the needle after the needle is positioned.

* * * * *